United States Patent [19]

Hounsell

[11] Patent Number: 4,604,360
[45] Date of Patent: Aug. 5, 1986

[54] CULTURE TRANSPORT APPARATUS

[76] Inventor: Melvin W. Hounsell, 1609 Sun Valley Dr., Beloit, Wis. 53511

[21] Appl. No.: 459,049

[22] Filed: Jan. 19, 1983

[51] Int. Cl.[4] .......... C12M 1/00; C12M 1/28; C12M 1/30; B01J 7/00
[52] U.S. Cl. ................. 435/287; 435/294; 435/295; 422/236
[58] Field of Search ............ 435/287, 294, 295, 296, 435/297, 298, 299, 300, 301, 801, 807, 313; 422/236

[56] References Cited

U.S. PATENT DOCUMENTS

| | | | |
|---|---|---|---|
| 3,163,160 | 12/1964 | Cohen | 435/295 |
| 3,165,450 | 1/1965 | Scheidt | 435/298 |
| 3,248,302 | 4/1966 | Mackin | 435/298 |
| 3,450,129 | 6/1969 | Avery et al. | 435/295 |
| 3,773,035 | 11/1973 | Aronoff et al. | 435/295 |
| 3,913,564 | 10/1975 | Freshley | 128/759 |
| 4,012,203 | 3/1977 | Rosiere | 422/236 |
| 4,013,422 | 3/1977 | Spinner et al. | 422/211 |
| 4,014,748 | 3/1977 | Spinner et al. | 435/295 |
| 4,038,148 | 7/1977 | Miller et al. | 435/296 |
| 4,108,728 | 8/1978 | Spinner et al. | 435/292 |
| 4,129,483 | 12/1978 | Bochner | 435/301 X |
| 4,246,339 | 1/1981 | Cole et al. | 435/7 |
| 4,312,950 | 1/1982 | Snyder et al. | 435/295 |
| 4,546,086 | 10/1985 | Hounsell | 435/287 |

Primary Examiner—Robert J. Warden
Assistant Examiner—Cynthia Lee Foulke
Attorney, Agent, or Firm—Vernon J. Pillote

[57] ABSTRACT

A microbial culture transport apparatus comprising an open top receptacle having a first open-top culture device receiving area for receiving a culture sample and at least a second container retaining area, a cover for the receptacle, and a rupturable container in the second area containing a material for use in maintaining viability of a culture sample. Interengaging detents are provided on the receptacle and cover for releasably retaining the cover in a first position with the top wall of the cover spaced above the bottom of the receptacle to maintain the culture sample and rupturable container in their respective areas without rupturing the container, the interengaging detents being releasable on response to downward pressure on the cover to move down to a second position. A punch on the cover is operative when the cover is moved from its first and second position on the receptacle for rupturing the rupturable container to release the culture sustaining material therein and seals are provided on the cover and receptacle for sealing the areas in the receptacle from the outside atmosphere when the cover is in its second position.

27 Claims, 12 Drawing Figures

CULTURE TRANSPORT APPARATUS

BACKGROUND OF THE INVENTION

The treatment of many bacterial diseases in man and in lower animals requires the infecting organism to be isolated and identified. The identification of an infecting organism is sometimes achieved by collecting a sample from the ill patient or animal using a swab and sometimes by collecting a liquid sample from the ill patient. While the collecting of such samples generally presents no difficulty, the storage and/or transportation of the sample to the testing laboratory under conditions which require the sample to be viable and free from contamination upon arrival, does present serious problems. It is necessary to not only avoid contamination of the sample from other organisms, but to also provide an environment which will maintain viability of the microbial culture during the time it is being transported and stored prior to being tested in the laboratory.

Some organisms do not require a specific gaseous atmosphere, but should have a moistening agent or nutrient to maintain viability of the microbial sample during storage and transportation. Bacteria of the anaerobic or obligate type such as the bacilli of tetanus, gas gangrene, botulism and bacterioides require an oxygen deficient or oxygen free environment for proper growth and maintenance. Furthermore, there are other organisms which require a special gaseous atmosphere for proper growth. Thus gonococcus, meningococcus and brucella, require a carbon dioxide enriched atmosphere for proper growth.

In order to facilitate collection and transport of microbial samples, self-contained culture transport apparatus have heretofore been proposed in which a culture collecting depot and a culture sustaining means are provided in a transport container and arranged so that the culture sustaining means can be selectively activated after the culture sample is deposited in the culture collecting depot. Some prior microbial culture transport apparatus such as disclosed in U.S. Pat. Nos. 3,163,160; 3,450,129 and 4,312,950, provide a liquid nutrient or transport medium in a transport container. Some other culture transport apparatus such as disclosed in U.S. Pat. Nos. 3,773,035; 3,913,564; 4,012,203; 4,013,422; 4,014,748; 4,038,148 and 4,108,728 include a means which can be selectively activated to provide a suitable gaseous atmosphere in the transport container for sustaining the microbial sample. In U.S. Pat. No. 3,773,035, the gaseous atmosphere is provided by a rupturable container for pressurized gas. In U.S. Pat. Nos. 3,913,564; 4,012,203; 4,013,422; 4,038,148 and 4,108,728. the gaseous atmosphere is provided by a self-contained gas generator including a solid gas generating material and an activating liquid in a rupturable container. In U.S. Pat. Nos. 4,038,148 and 4,108,728, color indicator means is also provided in the transport apparatus to indicate the presence or absence of oxygen.

Many of the prior culture transport apparatus utilize tube type transport containers which required assembly of several components in a predetermined sequence through an end of the tube. This increased the time and cost of assembly of such transport apparatus. In addition, some tube type transport containers were formed of a readily deformable plastic to facilitate rupturing one or more glass ampoules inside the tube containing a nutrient, an activating liquid for the gas generator, or a redox color indicating liquid. In use, glass fragments or shards from a ruptured ampoule sometimes pierced the deformable tube and caused injury to the user and/or loss of the atmospheric sustaining integrity of the transport container.

In U.S. Pat. Nos. 4,012,203; 4,013,422 and 4,038,148, a self-contained gas generating apparatus and/or redox color indicating apparatus and culture retaining receptacle are provided in a flexible bag or pouch. However, such bags or pouches are difficult to reseal after use and are easily ruptured during activation and transport of the apparatus.

U.S. Pat. No. 3,248,302 discloses a petri dish and in which the lid has a membranous sealing flange arranged to form a seal with the dish when the lid is closed, and a capsule containing a reducing agent or other chemicals or agents for use in effecting oxygen absorption or other desired atmospheric condition in the petri dish.

SUMMARY OF THE INVENTION

Although the prior art discloses microbial culture apparatus which can be selectively activated to provide an environment for maintaining the viability of a microbial sample, there is a need for a microbial culture apparatus which is more convenient, economical and efficient to produce and use.

Various important objects of this invention are to provide a microbial culture transport apparatus which can be easily and economically assembled and produced; which can be easily and efficiently closed and activated; and which effectively avoids injury to the user.

According to one aspect of the present invention there is provided a microbial culture transport apparatus comprising an open top receptacle, a culture receiving device having a plug member at the end, an opening in the side wall of the receptacle and a first open-top culture device receiving area at a first area of the bottom wall contiguous to said opening for receiving the culture receiving device when the plug member is positioned in said opening in the receptacle side wall, the receptacle having at least a second open-top container retaining area at a second area of the bottom wall, a cover for the receptacle, a rupturable container in the second area containing a material for use in maintaining viability of a culture sample, interengaging detent means on the receptacle and cover for releasably retaining the cover in a first position with the top wall of the cover spaced above the bottom of the receptacle to maintain the culture sample and container in their respective areas without rupturing the container, the interengaging detent means being releasable on response to downward pressure on the cover to move down to a second position, a means operative when the cover is moved from its first and second position on the receptacle for rupturing the rupturable container to release the culture sustaining material therein, and means on the cover and receptacle for sealing the areas iin the receptacle from the outside atmosphere when the cover is in its second position.

According to another aspect of the present invention, an anaerobic microbial culture apparatus is provided including a receptacle having a first culture device receiving area at a first area of the bottom wall for receiving a microbial sample and second and third open-top container retaining areas at respective second and third areas of the bottom wall, a rupturable container in the second area containing a material for providing a gaseous atmosphere in the receptacle, a rupturable container in the third area containing a redox color indicator liquid, a cover for the receptacle, means for releasably supporting the cover in a first position on the receptacle with the top wall of the cover positioned to retain the rupturable containers in the respective areas without rupturing the same, the detent means being releasable in response to downward pressure on the cover to allow the cover to move to a second position, means operative when the cover is moved from its first position to its second position for rupturing the rupturable containers, and means on the cover and receptacle engagable when the cover is in its second position for sealing the cover to the receptacle.

The culture transport apparatus can be more easily and economically assembled since the various components can be positioned in the respective areas through the open top of the receptacle. The microbial culture apparatus is also easier to use since it can be closed and activated in a single operation by pressing the cover downwardly to its second position and thereby rupturing the rupturable containers and sealing the cover to the receptacle. In addition, the culture transport apparatus effectively avoids problems sometimes encountered with prior microbial culture apparatus of the type in which the ampoules are positioned in a flexible plastic tube so that they can be ruptured by squeezing the tube, and wherein shards or pieces of the ampoule sometimes pierce the tube and cause injury to the user.

These, together with other objects, features and advantages of this invention will be more readily understood by reference to the following detailed description taken in conjunction with the accompanying drawings wherein:

The aerobic microbial culture apparatus of FIGS. 1-4 is adapted for collecting and transporting culture specimens which do not require a specific atmosphere, but which should be maintained moist or provided with a nutrient or transport medium, to maintain viability of the culture during the interval between collection of the culture and testing of the culture in a laboratory. The microbial culture apparatus includes an open top receptacle 20 having a bottom wall 21 and upstanding receptacle side wall means comprising upstanding side walls 22 and 23 and end walls 24 and 25 extending between the side walls. A cover 30 has a top wall 31 dimensioned to overlie the top of the receptacle and depending cover flange means comprising depending side flanges 32, 33 and end flanges 34, 35 adapted to extend downwardly along the side walls of the receptacle. The receptacle and cover are conveniently formed by molding of a rigid polymer or copolymer, for example Nylon, polycarbonate or polystyrene, to provide a shape sustaining receptacle and cover, and the receptacle cover is preferably formed of a transparent material.

Figures 1, 3, 4:
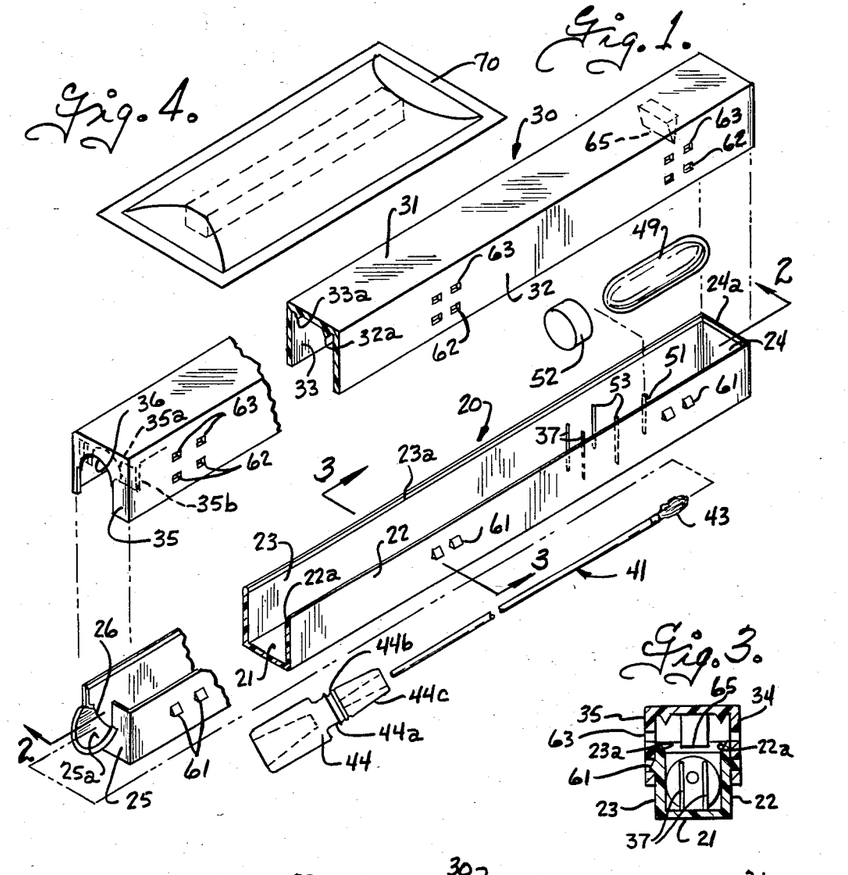
FIG. 1 is an exploded perspective view of an aerobic microbial culture transport apparatus embodying the present invention.
FIG. 3 is a transverse sectional view taken on the plane 3—3 of FIG. 1, with the components assembled in the receptacle and with the cover in a first position on the receptacle.
FIG. 4 is a perspective view of a package for transporting the aerobic culture transport apparatus of FIG. 1.
Figure 2:
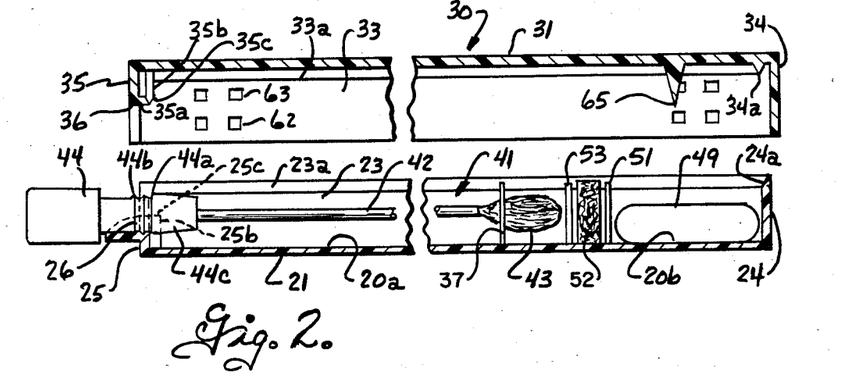
FIG. 2 is a longitudinal sectional view taken on the plane 2—2 of FIG. 1 and illustrating the components assembled in the receptacle and with the cover in a raised position.

A swab 41 is provided for collecting a culture and includes an elongated member 42, which may be formed of wood or plastic, with an absorbent swab tip 43 at one end and a plug member 44 at the other end providing a handle for the swab. The receptacle is elongated to receive the swab in a first open top culture device receiving area 20a at a first area of the bottom wall. The receptacle side wall means has an opening advantageously in the form of an upwardly opening notch or recess 26 in the end wall 25 to receive the plug member 44 on the swab when the swab is positioned in the area 20a. The cover 30 has a complimentary notch or recess 36 in the end wall 35 to extend around the plug member 44, when the cover is closed. The notches 26 and 36 are arranged to provide an opening sufficiently larger than the cross section of the swab tip to allow easy passage of the swab tip therethrough. Swab retaining means herein shown in the form of thin deformable or frangible pins or projections 37 are provided on the receptacle as by being molded integrally with the bottom wall, at locations to straddle the elongated member 42 adjacent the swab tip to position and releasably retain the swab in the receptacle when the cover is in its first position.

The culture apparatus carries a sealed supply of a transport media for moisturizing and/or providing nutrient for the culture, and the receptacle has a second open top container retaining area 20b at a second area of the bottom wall adjacent the end of the area 20a adjacent the swab tip. A rupturable ampoule 49 containing a suitable liquid nutrient or transport medium is positioned in the area 20b and is retained against endwise movement out of the area by a post 51. A pad of absorbent material 52, such as cotton or polyester, is positioned in the receptacle between the compartment 20a and the area 20b and is retained between the post 51 at the side adjacent the area 20b and by a pair of posts 53 at the side adjacent the area 20a. The ampoule 49 is formed of glass or other frangible or rupturable material which will permit release of the liquid transport or nutrient medium, and the plug 52 is arranged to absorb the liquid released from the ampoule. A transport medium in the rupturable container 49 may be any suitable liquid for supplying the moisture, electrolytes and/or nutrients required to maintain viability and/or growth as well as preventing organism desiccation of the culture for a suitable time interval, for example up to seventy-two hours. The culture transport media may, for example, be of the type described in U.S. Pat. No. 4,014,748.

The microbial culture apparatus is arranged so it can be preassembled with the swab, rupturable container and absorbent pad in the receptacle and the cover mounted on the receptacle, and thereafter activated to rupture the receptacle and seal the receptacle from outside atmosphere. A means is provided for releasably supporting the cover in a first position on the receptacle with the top wall of the cover spaced above the bottom of the receptacle a distance to retain the swab and rupturable container in their respective areas without rupturing the container, and to allow the cover to be pressed down to a second position in which it ruptures the rupturable container and seals the areas in the receptacle from communication with the outside atmosphere. For this purpose, interengaging detent means, herein shown in the form of protrusions 61 are provided, at spaced locations along the outer sides of the side walls of the receptacle, and sockets 62 are provided at corresponding spaced locations along the flanges of the cover. The protrusions 61 are arranged to extend into the sockets 62 to support the cover in a first position as shown in FIG. 3, with the top wall of the cover spaced above the upper edge of the side walls of the receptacle, and the protrusions are advantageously formed with a downwardly and outwardly inclined upper surface and a lower surface that extends at only slightly greater than 90° to the receptacle side wall. With this arrangement, the protrusions inhibit upward separation of the cover from the receptacle when they extend into the sockets 62, but function to cam the flanges on the cover outwardly when the cover is pressed downwardly. A second set of sockets 63 is provided in the cover flanges at a location spaced above the sockets 62, for receiving respective ones of protrusions 61 when the cover is moved down to a second position in which the top wall of the cover is contiguous to the upper edges of the side walls of the receptacle. Protrusions 61 cooperate with the sockets 63 to retain the cover in its second position.

Means are provided for rupturing the rupturable container 49 when the cover is moved from its first to its second position on the receptacle. For this purpose, a wedge shaped punch 65 is provided on the underside of the cover and may conveniently be formed integrally therewith. The punch 65 projects down from the top wall of the cover a distance such that it is spaced above the ampoule when the cover is in its first position as shown in FIG. 3, but will engage and rupture the container 49 when the cover is moved to its second position. The length of the punch 65 is preferably selected so that it only extends down from the top wall of the cover a distance sufficient to rupture the container when the cover is moved to its second position, without completely crushing the container which would increase the formation of glass fragments.

Provision is also made for sealing the cover to the receptacle when the cover is moved to its second position, to prevent loss of moisture and desiccation of the culture. The upper edges of the side walls 22, 23, and end wall 24 are formed with beveled surfaces 22a–24a respectively and the under side of the top wall 31 of the cover is provided with ribs 32a–34a that are spaced inwardly from the flanges 32–34 respectively and formed with beveled surfaces at their outer side generally complementary to the respective beveled surfaces 22a–24a on the side and end walls of the receptacle to engage and form a seal therewith when the cover is closed. A resilient sealing compound (not shown) such as resilient rubber or plastic compound is preferably applied as a thin coating on the surfaces 22a–24a respectively, to enhance the seal between the cover and the receptacle. The end wall 25 and the end flange 35 are arranged to form a seal with each other and with the plug member 44 of the swab, when the cover is in its closed position. For this purpose, the end wall 25 is formed with an upwardly opening generally semi-cylindrical wall portion 25a at the base of the notch 26 and which is dimensioned to receive an intermediate portion 44a on the plug member. Cylindrical wall portion 25a is advantageously arranged to project outwardly from the end wall 25 to facilitate reintroduction of the swab into the receptacle. The end flange 35 on the cover is formed with a downwardly opening generally semi-cylindrical wall portion 35a which is adapted to conform the upper side of the intermediate portion 44a of the swab handle to form a seal therewith when the cover is in its second position. The plug member 44 is preferably formed of a resilient deformable material, for example polyethylene, rubber or the like, and is provided with thin sealing ribs 44b on the intermediate portion 44a at a location to contact the walls 25a and 35a, to enhance the seal therebetween. Inner seal wall portions 25b are provided between the semi-cylindrical wall portions 25a and the adjacent side walls 22, 23 of the receptacle and are formed with a V-shaped upper seal surface 25c at a level adjacent the upper edge of the semi-cylindrical wall portion 25a. Similar inner seal wall portions 35b are provided on the cover inwardly of the end wall 35 and extend between the cylindrical wall portion 35a and the adjacent cover flange 32, 33 and are formed with a lower wedge shaped seal edge 35c cooperable with the upper seal 25c to form a seal between the cover and receptacle at opposite sides of the swab. The plug member 44 is formed with an inner end portion 44c that is larger in cross section than the intermediate portion to provide a shoulder or abutment means at the juncture with the intermediate portion for engaging the end wall 25 adjacent the notch to retain the swab against outward movement when the cover is in its second position. The inner portion 44c of the plug member is tapered in a direction toward the swab tip, to facilitate reintroduction of the swab into the receptacle after collecting a sample on the swab tip.

The culture transport apparatus is preferably sterilized and shipped in a sterile condition in an outer wrapper or package 70 as shown in FIG. 4. The outer wrapper 70 is conveniently formed with a back sheet of a gas permeable sheet material such as glassine, craft paper or Tyvek, and a top sheet of the same material or a clear low gas permeable film or sheet material which is bonded to the edge of the back sheet material, both sheets being of suitable porosity to maintain product sterility. By utilizing a gas permeable sheet for at least one of the sides of the wrapper or package 70, the packaging apparatus and the interior of the wrapper can be sterilized after sealing by subjecting the sealed package to a sterilizing gas such as ethylene oxide. Alternatively, the culture apparatus and package can be sterilized by radiation.

An anaerobic culture apparatus for collecting and transporting samples on a swab is shown in FIGS. 5–9.

Many parts of the anaerobic apparatus are the same or similar to those in the aerobic culture transport apparatus of FIGS. 1–4 and like numerals increased by 100 are used to designate corresponding parts. The receptacle 120 has a bottom wall 121, upstanding receptacle side wall means comprising side walls 122 and 123 and end walls 124 and 125. A cover 130 has a top wall 131 adapted to overlie the top of the receptacle and depending cover flange means comprising side flanges 132, 133 and end flanges 134, 135 adapted to extend downwardly along respective ones of the side and end walls of the receptacle. A swab 141 is provided for collecting a culture and includes an elongated member 142 having a swab tip 143 at one end a plug member 144 at its other end providing a handle. The swab is positioned in a first open-top culture device receiving area 120a at a first area of the bottom wall of the receptacle and one end wall 125 of the receptacle has an opening formed by an upwardly opening notch or recess 126 for receiving the handle portion of the swab when the swab is positioned in the area 120a. Deformable or frangible pins 137 are molded on the bottom wall of the receptacle at locations to straddle the elongated member 142 adjacent the swab tip to releasably retain the swab in the receptacle when the cover is in its first position. A rupturable container 149 containing a culture transport medium is positioned in a second open-top container retaining area 120b at a second area of the bottom wall of the receptacle and a pad 152 of absorbent material is positioned in the receptacle between the areas 120a and 120b. Endwise movement of the rupturable container 149 is inhibited by a locating post 151 and the pad 152 is laterally retained in position at one side by the post 151 and at the other side by spaced posts 153. Interengaging detents, including protrusions 161 on the outer sides of the side walls of the receptacle and sockets 162 on the side flanges 132, 133 on the cover, are provided for releasably supporting the cover in a first position in which the top wall is spaced above the upper edges of the side walls of the receptacle. The interengaging detents are releasable in response to downward pressure on the cover to allow the cover to move down to a second position in which the top wall of the cover is contiguous to the upper edges of the side walls of the receptacle. A second set of sockets 163 are provided on the side walls of the flanges to receive the protrusions 161 when the cover is moved to its second position, and thereby retaining the cover in that position. A projection or anvil 165 is provided on the underside of the cover for rupturing the container 149 when the cover is moved to its second position. Beveled seal surfaces 122a, 123a and 124a are provided on the walls 122–124 respectively and cooperate with seal ribs 132a, 133a and 134a provided on the underside of the top wall of the cover, to seal the cover to the side and end walls of the receptacle when the cover is in its second position. A resilient sealing compound (not shown) is preferably applied as a thin coating on the surfaces 122a–124a, to enhance the seal between the cover and receptacle. Semi-cylindrical wall surfaces 125a and 135a are provided on the end wall 125 of the receptacle and end flange 135 of the cover to cooperate with an intermediate portion 144a of the plug member, to form a seal with the plug member. As in the preceding embodiment, the plug member 144 is preferably formed of a resilient elastomeric material with thin deformable seal rings 144b on the intermediate portion 144a, to enhance the seal with the cover and receptacle. The plug member 144 has an inner end portion 144c that is larger in cross section than the intermediate portion 144a to provide a shoulder or abutment means for engaging the end wall 125 to retain the swab against outward movement under gas pressure when the cover is in its second position. The inner end portion 144c is tapered to facilitate reintroduction of the swab into the receptacle after collecting a sample on the swab tip. Inner seal walls 125b are provided in the receptacle adjacent the end wall 125 and are formed with a V-shaped upper seal surface 125c, and inner seal walls 135b are provided in the cover inwardly of the end wall 135 and have a wedge-shaped lower seal face 135c, arranged to engage and seal against the seal face 125c, when the cover is in its second position, to form a seal across the end of the cover and receptacle at opposite sides of the swab handle.

The anaerobic culture apparatus includes means for providing a preselected gaseous atmosphere in the culture receiving area 120a and a means for indicating the presence or absence of oxygen in the culture receiving area. In this embodiment, the receptacle has a third open-top container retaining area 120c at a third area of the bottom wall for receiving a container of material to provide a gaseous atmosphere and a fourth open-top container retaining area 120d at a fourth area of the bottom wall for receiving a container of color indicator liquid. A partition wall 180 is provided in the receptacle between the side walls 122 and 123 and separates the areas 120a and 120b which are located at one side of the partition wall from areas 120c and 120d which are located at the other side of the partition wall and the partition wall has openings 180a at spaced locations therealong at a level above the bottom wall of the receptacle to communicate the areas 120c and 120d with the area 120a. A rupturable container 181, containing a material for use in providing a desired gaseous atmosphere in the receptacle, is positioned in the area 120c and retained against endwise movement by a pin or post 182 conveniently formed integrally with the bottom wall of the receptacle. The means for providing a gaseous atmosphere can be a gas generating apparatus which includes a solid gas generating material and a liquid in a rupturable container for reacting with the solid gas generating material to produce the desired gaseous atmosphere, for example as disclosed in U.S. Pat. Nos. 4,012,203 and 4,013,422, to which reference is made for a more detailed disclosure. If a gas generating apparatus is used, then the rupturable container 181 would contain a liquid that is reactive with a solid gas generating material (not shown) positioned in the third area 120c. However, the solid gas generating materials are generally deliquescent and, to avoid the problems encountered with deterioration of the solid gas generating material prior to use, the container 181 preferably includes the gas or mixture of gasses under pressure which, when released, will produce the desired gaseous atmosphere in the culture receiving areas 120a. The container may, for example, include a reducing gas such as hydrogen or acetylene, or a reducing gas in combination with a culture sustaining gas such as carbon dioxide. The container 181 can be formed of a rupturable glass or plastic, or of a thin metal which can be punctured, or it can be a rigid container having at least one area or plug which is rupturable as by puncturing or piercing. A punch 168 is provided on the underside of the cover 130 and has a length such that it is spaced above the rupturable container 181 when the cover is in its first position on the receptacle, but will engage and pierce or rupture the container, when the cover is moved down to its second position.

Figures 5, 6:
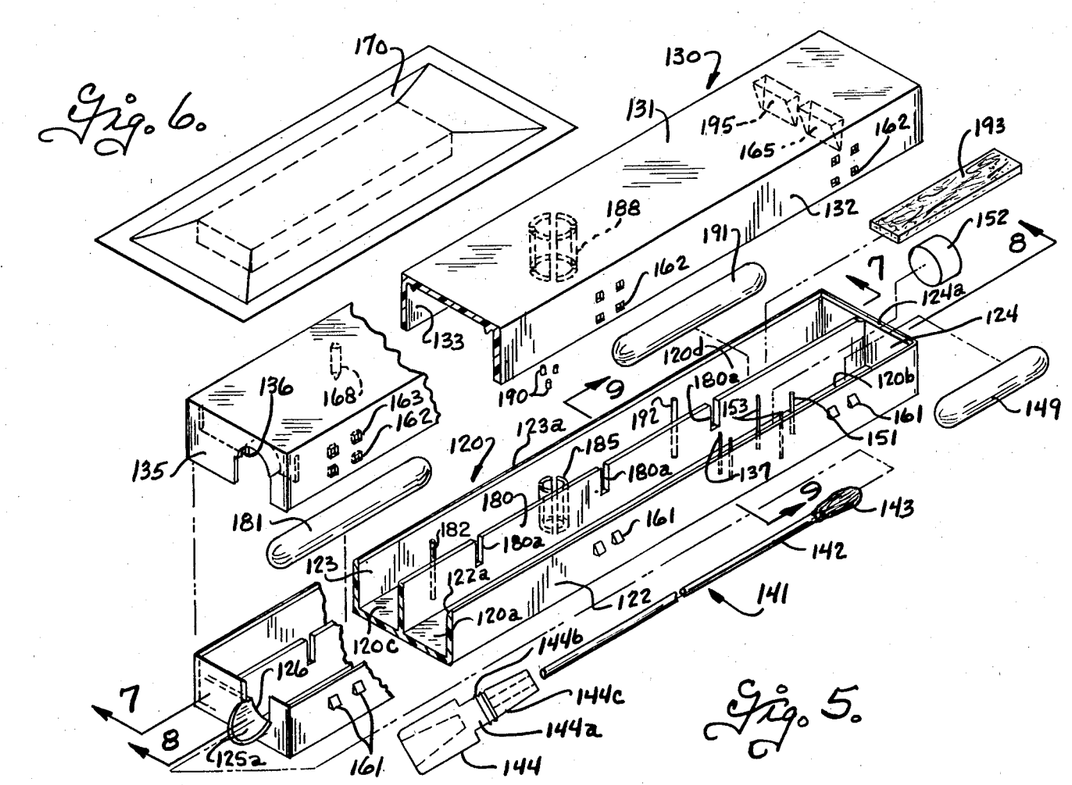
FIG. 5 is an exploded perspective view of an anaerobic microbial culture transport apparatus embodying the present invention.
FIG. 6 is a perspective view of a package for transporting the microbial culture transport apparatus of FIG. 5.
Figure 7:
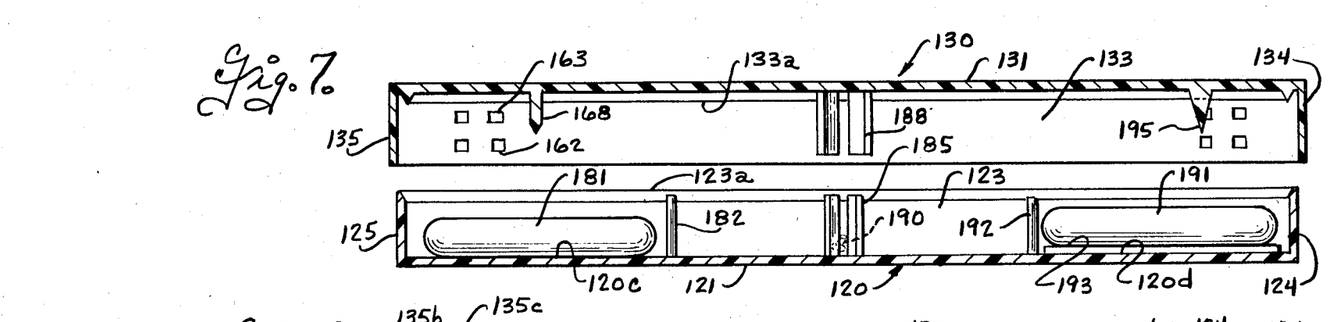
FIG. 7 is a longitudinal sectional view taken on the plane 7—7 of FIG. 5, with the components assembled in the base receptacle and with the cover raised.

A catalyst is advantageously provided for inducing the reaction of the reducing gas with oxygen in the receptacle. A 5% palladium-on-alumina catalyst may be used, although other catalysts which induce a reducing gas to react with oxygen at room temperature may be employed. The catalyst which is in the form of one or more small porous pellets 190 is preferably maintained in a small catalyst chamber 185 that communicate with the areas 120c and 120d. The catalyst chamber is formed integrally with the receptacle and, as best shown in FIGS. 5 and 7, the catalyst chamber is located on an area of the receptacle bottom wall that is intermediate the compartments 120c and 120d. In order to facilitate molding, the catalyst chamber is preferably in the form of a segmented upright cylinder that is open at its top and with the spaces between the segments defining vent passages to communicate the catalyst chamber with the interior of the receptacle including areas 120c and 120d. A means is provided on the cover for retaining the catalyst pellets in the catalyst chamber when the cover is in either its first or its second position. The catalyst retaining means is formed integrally with the cover and, to facilitate molding, is in the form of a segmented cylindrical sleeve 188 arranged to telescopically engage the catalyst chamber 185, to allow movement of the cover between its first and second position while retaining the pellets in the catalyst chamber. The slots between the segments in the retainer sleeve 188 are preferably arranged to register with the slots in the catalyst chamber 185 to maintain open communication between the catalyst chamber and the areas 120c and 120d when the cover is in its second position.

Figure 8:
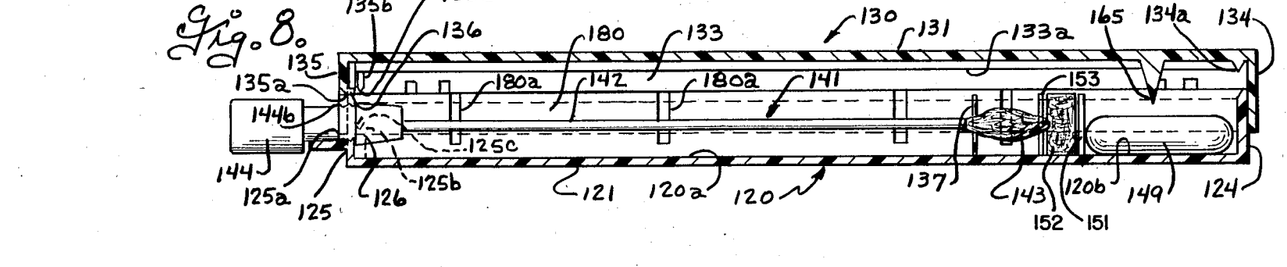
FIG. 8 is a longitudinal sectional view taken on the plane 8—8 of FIG. 5 with the components assembled.
Figure 9:
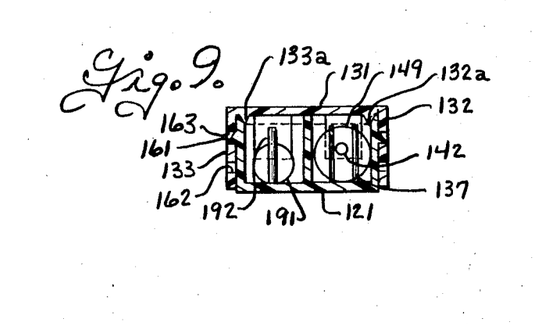
FIG. 9 is a transverse sectional view taken on the plane 9—9 of FIG. 5, and illustrating the parts with the cover in its closed condition.

A rupturable container 191 containing a redox color indicator liquid is positioned in the fourth area 120d and is retained against endwise movement in that area as by a post 192 conveniently molded integrally with the bottom wall of the receptacle. The redox color indicator liquid may be selected from any suitable material which will reversibly change color when the atmosphere around it changes from one which is oxygen deficient to one where there is a significant or substantial amount of oxygen in the atmosphere and vice versa. The color indicator liquid may, for example, be a 0.001% solution of resazurin in water. This indicator is colorless in an oxygen free atmosphere and is pink in an oxygen containing atmosphere. The container 191 may be an ampoule of glass or plastic which is rupturable when compressed. An absorbent pad 193 of a nonwoven polyester material is provided for absorbing the color indicator when the ampoule is ruptured and preferably underlies the ampoule in the receptacle. A means such as a punch 195 is provided on the cover at a location to engage and rupture the container 191 when the cover is moved from its first to its second position.

The anaerobic culture apparatus is also preferably sterilized and packaged in an outer wrapper or package 170. The package 170 and the anaerobic culture apparatus are sterilized either before or after sealing of the package, as by a sterilizing gas such as ethylene oxide or by radiation, so that the anaerobic culture apparatus and its contents remain sterile until the package 170 is opened at the time of use.

The manner in which the aerobic culture apparatus of FIGS. 1–4 and an anaerobic culture apparatus of FIGS. 5–9 are used is similar. The culture apparatus is fully assembled and ready for use with the cover in its first position, when the culture apparatus are removed from the outer package or wrapper. The swab is removed from the receptacle by pulling outwardly on the swab handle, while the cover remains in its first position. A culture is then collected on the swabbing tip and the swab is immediately reinserted back into the receptacle through the opening in the end wall to a point where the swab tip contacts the absorbent medium pad, and with the plug member extending into the opening in the end wall of the receptacle. The apparatus is then activated by placing the apparatus on a solid surface, cover up, and pressing down with both thumbs or the palms of the hand to cause the cover to move down to its second position. This effects sealing of the cover to the receptacle and to the plug member. In addition, movement of the cover from its first to its second position ruptures the rupturable container or containers in the receptacle. The aerobic culture apparatus has a rupturable container 49 containing a transport and/or nutrient medium to maintain viability of the culture. The anaerobic culture apparatus additionally contains rupturable containers for providing a desired gaseous atmosphere in the receptacle and for also indicating the oxygen or lack of oxygen in the receptacle.

Figures 10, 11, 12:
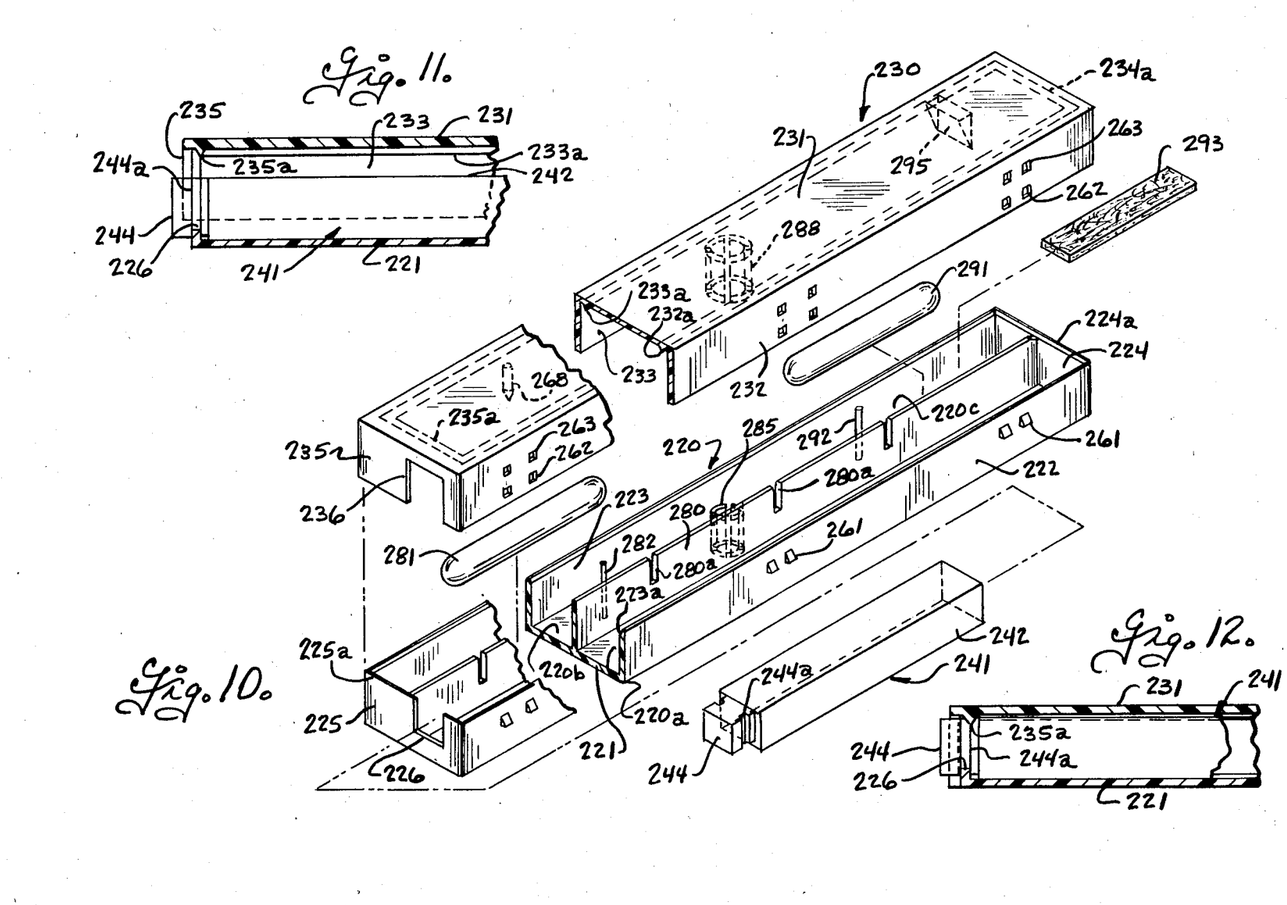
FIG. 10 is an exploded perspective view of an anaerobic microbial culture transport apparatus for liquid samples.
FIG. 11 is a fragmentary longitudinal sectional view taken on the plane 11—11 of FIG. 10, showing the cover in a raised position on the receptacle.
FIG. 12 is a fragmentary longitudinal sectional view taken on the plane 11—11 of FIG. 10 and showing the cover in its closed position.

An anaerobic culture transport apparatus transporting liquid sample is shown in FIGS. 10–12. Many parts of the liquid culture transport apparatus of FIGS. 10–12 are the same or similar to those in the anaerobic culture transport apparatus of FIGS. 5–9 and like numerals increased by 100 are used to designate corresponding parts. The receptacle 220 has a bottom wall 221, upstanding receptacle side wall means comprising side walls 222 and 223 and end walls 224 and 225. A cover 230 has a top wall 231 adapted to overlie the top of the receptacle and depending cover flange means comprising side flanges 232, 233 and end flanges 234, 235 adapted to extend downwardly along respective ones of the side and end walls of the receptacle. A liquid retaining container 241 is provided for receiving a liquid culture sample and includes a liquid receiving bag 242 having a plug member 244 at one end. The bag 242 is positioned in a first open-top culture device receiving area 220a at a first area of the bottom wall of the receptacle and one end wall 225 of the receptacle has an opening formed by an upwardly opening notch or recess 226 for receiving the plug member on the liquid retaining container when it is positioned in the area 220a. The bag 242 of the liquid retaining container is formed of a material that is liquid retaining but gas permeable, for example a silicone rubber membrane to allow gas transfer between the bag and the interior of the receptacle. The bag can be formed separate from the plug member and sealed thereto to form a closed container or, alternatively, the bag 242 can be molded as a sleeve integrally with the plug member and thereafter sealed at the end remote from the plug member. The plug member 244 is formed of an elastomeric material such as rubber which can be readily penetrated by the needle of a syringe, but which is self-sealing after withdrawal of the needle. Alternatively, the plug member can be provided with a liquid access opening which is closable by a stopper.

Interengaging detents, including protrusions 261 on the outer sides of the side walls of the receptacle and sockets 262 on the side flanges 232, 233 on the cover, are provided for releasably supporting the cover in a first position in which the top wall is spaced above the upper edges of the side walls of the receptacle. The interengaging detents are releasable in response to downward pressure on the cover to allow the cover to move down to a second position in which the top wall of the cover is contiguous to the upper edges of the side walls of the receptacle. A second set of sockets 263 are provided on the side walls of the flanges to receive the protrusions 261 when the cover is moved to its second position, to thereby retain the cover in that position. Beveled seal surfaces 222a, 223a, 224a and 235a are provided on the walls 222-224 respectively and cooperate with seal ribs 232a, 233a, 234a and 235a provided on the underside of the top wall of the cover, to seal the cover to the side and end walls of the receptacle when the cover is in its second position. A resilient sealing compound (not shown) is preferably applied as a thin coating on the surfaces 222a-224a, to enhance the seal between the cover and receptacle. The plug member 244 is a resilient elastomeric material and is provided with recesses 244a along its sides and bottom to receive the end wall 225 of the receptacle adjacent the notch 226 therein to form a seal with the end wall of the receptacle and provide an abutment means to retain the plug member and bag 242 against outward movement under gas pressure when the cover is in its second position. The upper side of the plug member 244 may be made flat as shown to engage the rib 235a at the underside of the cover when the latter is in its closed position and form a seal therewith.

The anaerobic liquid transport apparatus includes means for providing a preselected gaseous atmosphere in the culture receiving area 220a and a means for indicating the presence or absence of oxygen in the culture receiving area. In this embodiment, the receptacle has a second open top container retaining area 220b at a second area of the bottom wall for receiving a second container and a third open top container retaining area at a third area of the bottom wall for receiving a third container. A partition wall 280 is provided in the receptacle between the side walls 222 and 223 and separates the area 220a which is located at one side of the partition wall from areas 220b and 220c located at the other side of the partition wall and the partition wall has openings 280a at spaced locations therealong at a level above the bottom wall of the receptacle to communicate the areas 220b and 220c with the area 220a. A rupturable container 281, containing a material for providing a desired gaseous atmosphere in the receptacle, is positioned in the area 220b and retained against endwise movement by a pin or post 282 conveniently formed integrally with the bottom wall of the receptacle. The container 281 preferably includes the gas or mixture of gasses under pressure which, when released, will produce the desired gaseous atmosphere in the culture compartment 220a. The container may, for example, include a reducing gas such as hydrogen or acetylene, or a reducing gas in combination with a culture sustaining gas such as carbon dioxide. Alternatively, a gas generating apparatus can be provided as previously described in connection with the embodiment of FIGS. 5-9. The container 281 can be formed of a rupturable glass or plastic, or of a thin metal which can be punctured, or it can be a rigid container having at least one area or plug which is rupturable as by puncturing or piercing. A punch 268 is provided on the underside of the cover 230 and has a length such that it is spaced above the rupturable container 281 when the cover is in its first position on the receptacle, but will engage and pierce or rupture the container, when the cover is moved down to its second position.

A catalyst is advantageously provided for inducing the reaction of the reducing gas with oxygen in the receptacle. A 5% palladium-on-alumina catalyst may be used, although other catalysts which induce a reducing gas to react with oxygen at room temperature may be employed. The catalyst which is in the form of one or more small porous pellets 290 is preferably maintained in a small catalyst chamber 285 that communicates with the interior of the receptacle including the areas 220b and 220c. The catalyst chamber is formed integrally with the receptacle and, in order to facilitate molding, is preferably in the form of a segmented upright cylinder that is open at its top and with the spaces between the segments defining vent passages to communicate the catalyst chamber with the interior of the receptacle including 220b and 220c. As best shown in FIG. 10, the catalyst chamber is located on an area of the receptacle bottom wall that is intermediate the areas 220b and 220c. A means is provided on the cover for retaining the catalyst pellets in the catalyst chamber when the cover is in either its first or its second position. The catalyst retaining means is formed integrally with the cover and, to facilitate molding, is in the form of a segmented cylindrical sleeve 288 arranged to telescopically engage the catalyst chamber 285, to allow movement of the cover between its first and second position while retaining the pellets in the catalyst chamber. The slots between the segments in the retainer sleeve 288 are preferably arranged to register with the slots in the catalyst chamber 285 to maintain open communication between the catalyst chamber and the compartments 220b and 220c when the cover is in its second position.

A rupturable container 291 containing a redox color indicator liquid is positioned in the area 220c and is retained against endwise movement in that area as by a post 292 conveniently molded integrally with the bottom wall of the receptacle. The redox color indicator liquid may be of the type previously described in connection with FIGS. 5-9. The container 291 may be an ampoule of glass or plastic which is rupturable when compressed. An absorbent pad 293 of a nonwoven polyester material is provided in the compartment 220c for absorbing the color indicator when the ampoule is ruptured and preferably underlies the ampoule in the receptacle. A means such as a punch 295 is provided on the cover at a location to engage and rupture the container 291 when the cover is moved from its first to its second position. The anaerobic liquid culture transport apparatus is also preferably sterilized and packaged in an outer wrapper or package as previously described in connection with FIGS. 1-4 and 5-9.

The liquid culture transport apparatus is fully assembled and ready for use with the cover 230 in its first position on the receptacle 220, when the liquid culture transport apparatus is removed from its outer package or wrapper. The liquid culture transport apparatus is activated by placing the apparatus on a solid surface, cover up, and pressing down with both thumbs or the palms of the hand to cause the cover to move down to its second position. This effects sealing of the cover to the receptacle and to the plug member 244. In addition, movement of the cover from its first to its second position ruptures the rupturable containers 281 and 291 in the receptacle. Rupturing of rupturable container 281 releases a gas for catalytically reacting with the oxygen in the receptacle and for providing a desired gaseous atmosphere. The gas permeable membrane of container 241 allows gas to pass from outside to inside the container 241 and vice versa, until the atmosphere in the container 241 reaches substantial equilibrium with the atmosphere in the receptacle to thereby provide the desired gaseous atmosphere in the container 241. Rupturing of rupturable container 291 releases a color indicator liquid which is absorbed by pad 293 to provide a visual indicator of the presence or lack of oxygen in receptacle. The liquid culture transport apparatus is preferably activated some time, for example 20 to 30 minutes, prior to introduction of the liquid sample into the container 241, to allow time for the gaseous atmosphere in the receptacle and container 241 to reach substantial equilibrium. The liquid sample is then introduced into the container 241, as by inserting the needle of a syringe through the plug member 244. The needle is withdrawn from the plug member after introduction of the sample, and the elastomeric plug member is arranged to reseal the opening formed by the needle.

The culture transport apparatus in the present invention markedly facilitates assembly of the various components into the receptacle since they can be positioned through the open top of the receptacle into the appropriate area, instead of having to be serially inserted into an end of a tube as in prior culture apparatus having a tubular housing. The culture transport apparatus also facilitates use of the apparatus since it is closed and activated by pressing the cover down from its first to its second position. This avoids the necessity of having to sequentially rupture different rupturable containers in prior tube type culture apparatus. In addition, the culture apparatus enables use of a rigid walled receptacle and cover and this effectively prevents pieces or shards of the ampoules from puncturing the container, as sometimes occurred in prior flexible tube type culture apparatus.

The embodiments of the invention in which an exclusive property or privilege is claimed are defined as follows:

1. A culture transport apparatus comprising, an open top receptacle having a bottom wall and upstanding side wall means, a cover having a top wall and depending cover flange means adapted to extend downwardly along the side wall means of the receptacle, a culture receiving device having a plug member at one end, the side wall means of the receptacle having a recess therein, the receptacle having a first open top culture device receiving area at one area of the bottom wall contiguous to said recess in the side wall means for receiving the culture receiving device when the plug member is positioned in said recess in the side wall means, the receptacle having a second open top container retaining area at a second area of the bottom wall and communicating with the first culture device receiving area, a rupturable container in said second container retaining area containing a material for use in maintaining viability of a microbial sample, interengaging detent means on the receptacle side wall means and cover flange means for releasably retaining the cover in a first position on the receptacle with the top wall of the cover spaced above the bottom wall of the receptacle to maintain the culture receiving device and rupturable container in the respective first culture device receiving area and second container retaining area without rupturing the rupturable container, the interengaging detent means being releasable in response to downward pressure on the cover to allow the cover to move down to a second position, means operative when the cover is moved from its first to its second position on the receptacle for rupturing the rupturable container to release the material therein, the cover flange means having a recess therein at a location to form an opening with the recess in the side wall means of the receptacle when the cover is on the receptacle, and means on the cover and receptacle for sealing the first culture device receiving area and second container retaining area in the receptacle from outside atmosphere when the cover is in said second position.

2. A culture transport apparatus according to claim 1 wherein said detent means includes means for retaining said cover in said second position on the receptacle.

3. A culture transport apparatus according to claim 1 wherein said culture receiving device is a swab including an elongated member having swab tip at one end and said plug member at the other end.

4. A culture transport apparatus according to claim 3 including swab retainer means on the receptacle engaging the elongated member adjacent the swab tip for releasably retaining the swab in said first culture device receiving area, the swab retainer means being deformable to allow passage of the swab tip when the swab is axially withdrawn from the receptacle.

5. A culture transport apparatus according to claim 3 wherein said material in the rupturable container is a culture sustaining liquid, said culture transport apparatus also including a pad of absorbent material, and means for locating the pad in the culture transport apparatus at a position to absorb culture sustaining liquid when the container is ruptured and to contact the swab tip.

6. A culture transport apparatus according to claim 1 wherein the rupturable container contains a material for use in providing a preselected gaseous atmosphere in the first culture device receiving area.

7. A culture transport apparatus according to claim 1 wherein said culture receiving device is a closed liquid retaining container having at least a portion formed of a gas permeable material, said plug member being formed of a resilient deformable material.

8. A culture transport apparatus according to claim 1 wherein said plug member of the culture receiving device is formed of a resilient deformable material.

9. A culture transport apparatus according to claim 1 wherein the side wall means has a beveled surface along its upper edge, said cover having a beveled surface at the underside of the top wall complementary to and engageable with the beveled surface on the side wall means when the cover is in its second position for sealing the cover to the receptacle.

10. A culture transport apparatus according to claim 1 wherein said side wall means has a beveled surface along the inner side of its upper edge, said cover having a rib at the underside of the top wall spaced inwardly from the flange means and having a beveled surface along the outer face of the rib engageable with the beveled surface in the side wall means when the cover is in its second position for sealing the cover to the receptacle.

11. A culture transport apparatus according to claim 10 including a coating of a resilient sealing material on its beveled surface on the side wall means.

12. A culture transport apparatus according to claim 1 wherein said interengaging detent means includes a plurality of protrusions at spaced locations on the outer side of the side wall means of the receptacle, and a plurality of lower sockets at spaced locations in the inner side of the flange means of the cover arranged to receive corresponding ones of the protrusions when the cover is in said first position and a plurality of upper sockets at spaced locations in the inner side of the flange means on the cover arranged to receive corresponding ones of the protrusions when the cover is in said second position.

13. A culture transport apparatus comprising a receptacle having a bottom wall and upstanding side wall means, a cover having a top wall and depending cover flange means adapted to extend downwardly along the side wall means of the receptacle, a culture receiving device having a plug member at one end, the side wall means of the receptacle having a recess therein, the receptacle having a first open top culture device receiving area at one area of the bottom wall contiguous to said recess in the side wall means for receiving the culture receiving device when the plug member is positioned in said recess in the side wall means, the receptacle having a second open top container retaining area at a second area of the bottom wall and communicating with the first culture device receiving area, a rupturable container in said second container retaining area containing a material for use in maintaining viability of a microbial sample, means for releasably retaining the cover in a first position on the receptacle with the top wall of the cover spaced a first distance above the bottom wall of the receptacle sufficient to retain the culture retaining device and rupturable container in the first culture device receiving area and second container retaining area without rupturing the rupturable container, said last mentioned means being releasable in response to downward pressure on the cover to allow the cover to move down to a second position in which the top wall is spaced a second relatively shorter distance from the bottom wall, the cover flange means having a recess therein at a location to form an opening with the recess in the side wall means of the receptacle when the cover is on the receptacle, means operative when the cover is moved from its first to its second position on the receptacle for rupturing the rupturable container to release the material therein, means on the cover and receptacle for sealing the cover to the receptacle around said first culture device receiving area and second container retaining area when the cover is in its second position, and means on the cover flange means and receptacle side wall means for forming a seal with the plug member on the culture retaining device when the cover is in its second position.

14. A culture transport apparatus according to claim 13 wherein the material in the container is culture sustaining liquid, said receptacle has a third open top container retaining area at a third area of the bottom wall and communicating with said first culture device receiving area, a second rupturable container positioned in said third container retaining area, the second container containing a material for use in providing a gaseous atmosphere, and means operative in response to movement of the cover from its first to its second position for rupturing said second rupturable container.

15. A culture transport apparatus according to claim 14 wherein the material in the second container provides at least a reducing gas, said receptacle has means defining a catalyst chamber open at its upper end and communicating with said third container retaining area, at least one catalyst pellet in the catalyst chamber which promotes reaction between the reducing gas and oxygen in the receptacle, and means on the cover cooperable with the means defining the catalyst chamber for maintaining the catalyst pellet in the catalyst chamber when the cover is in its first and its second position.

16. A culture transport apparatus according to claim 15 wherein the receptacle has a fourth open top container retaining area at a fourth area of the bottom wall and communicating with said first culture device receiving area, a third rupturable container positioned in the fourth container retaining area containing a redox color indicator liquid, and means operable in response to movement of the cover from its first to its second position for rupturing the third rupturable container.

17. A culture transport apparatus according to claim 13 wherein said receptacle has a third open top container retaining area at a third area of the bottom wall and a fourth open top container retaining area at a fourth area of the bottom wall, said receptacle having partition wall means and said first container receiving area and second container retaining area being located at one side of the partition wall means and said third and fourth container retaining areas being located at the other side of said partition wall means, said partition wall means having openings for communicating the second and third container retaining areas with the first culture device receiving area, means in the receptacle defining a catalyst chamber on an area of the bottom wall at said other side of the partition wall means and intermediate said third and fourth container retaining areas, the catalyst chamber having vent passages for communicating the catalyst chamber with the interior of the receptacle, a second rupturable container in the third container retaining area containing a material for providing a gaseous atmosphere including at least a reducing gas, a catalyst in the catalyst chamber which promotes reaction between the reducing gas and oxygen in the receptacle, a third rupturable container in the fourth container retaining area containing a redox color indicator liquid, and means operative when the cover is moved from its first to its second positions for rupturing said second and third rupturable containers.

18. A culture transport apparatus according to claim 13 wherein the material in the container is a gas for providing a gaseous atmosphere in the receptacle when the container is ruptured.

19. A culture transport apparatus according to claim 18 including abutment means on the plug member of the culture receiving device engageable with the side wall means of the receptacle for holding the plug member against endwise movement in response to gas pressure in the container.

20. A culture transport apparatus according to claim 13 wherein the material in the container provides at least a reducing gas, said receptacle has means defining a catalyst chamber open at its upper end and communicating with said second container retaining area, at least one catalyst pellet in the catalyst chamber which promotes reaction between the reducing gas and oxygen in the receptacle, and means on the cover telescopically engageable with the means defining the catalyst chamber for maintaining the catalyst pellet in the catalyst chamber when the cover is in its first and its second position.

21. A culture transport apparatus according to claim 13 wherein the receptacle has means defining a third container retaining area at a third area of said bottom wall and communicating with said first culture device receiving area, the material in the container in the second container retaining area providing at least a reducing gas, a second rupturable container positioned in the third container retaining area containing a redox color indicator liquid, and means operable in response to movement of the cover from the first to its second position for rupturing the second rupturable container.

22. A culture transport apparatus according to claim 13 wherein the rupturable container contains a material for use in providing a preselected gaseous atmosphere in the first culture device receiving area, and said culture receiving device is a liquid retaining container having at least a portion formed of a gas permeable material, said plug member being formed of a resilient deformable material.

23. A culture transport apparatus according to claim 13 including means for retaining said cover in said second position on the receptacle.

24. An anaerobic culture transport apparatus comprising an open top receptacle having a bottom wall and upstanding side and end walls, the receptacle having a first open top culture device receiving area at a first area of the bottom wall for receiving a microbial sample and at least second and third open top container retaining areas at respective second and third areas of the bottom wall and each communicating with said first culture device receiving area, a first rupturable container in the second container retaining area containing a material for use in providing a gaseous atmosphere in the container, a second rupturable container in the third culture device receiving area containing a redox color indicator liquid and an absorbent pad, a cover having a top wall and depending flange means adapted to extend downwardly along the side wall means, detent means for releasably supporting the cover in a first position on the receptacle with the top wall of the cover spaced above the bottom wall of the receptacle a distance to retain the first and second rupturable containers in the second and third container retaining areas without rupturing the containers, the detent means being releasable in response to downward pressure on the cover to allow the cover to move down to a second position, said detent means including means for retaining the cover in said second position on the receptacle, means operative when the cover is moved from its first position to its second position on the receptacle for rupturing said first and second rupturable containers, and means on the cover and receptacle engageable when the cover is in its second position for sealing the cover to the side wall means of the receptacle.

25. A culture transport apparatus according to claim 24 wherein the material in the first container is a gas.

26. A culture transport apparatus according to claim 24 wherein the material in the first container provides at least a reducing gas, said receptacle has means defining a catalyst chamber open at its upper end and communicating with said second container retaining area, at least one catalyst pellet in the catalyst chamber which promotes reaction between the reducing gas and oxygen in the receptacle, and means on the cover telescopically engageable with the means defining the catalyst chamber for maintaining the catalyst pellet in the catalyst chamber when the cover is in its first and its second positions.

27. A culture transport apparatus according to claim 26 wherein the receptacle includes a fourth container retaining area in a fourth area of the bottom wall and communicating with said first culture device receiving area, a third rupturable container containing a culture nutrient medium in said fourth container retaining area, and means on the cover for rupturing the third rupturable container when the cover is moved from its first to its second position.

* * * * *